United States Patent [19]
Miyata et al.

[11] Patent Number: 5,985,858
[45] Date of Patent: Nov. 16, 1999

[54] PHOSPHONIC DIESTER DERIVATIVES

[75] Inventors: Kazuyoshi Miyata; Yasuhiro Sakai; Yasuo Shoji; Yoshihiko Tsuda; Yasuhide Inoue; Keigo Sato, all of Naruto; Shinya Miki, Tokushima, all of Japan

[73] Assignee: Otsuka Pharmaceutical Factory, Inc., Tokushima, Japan

[21] Appl. No.: 09/091,946

[22] PCT Filed: Dec. 24, 1996

[86] PCT No.: PCT/JP96/03775

§ 371 Date: Jun. 26, 1998

§ 102(e) Date: Jun. 26, 1998

[87] PCT Pub. No.: WO97/24360

PCT Pub. Date: Jul. 10, 1997

[30] Foreign Application Priority Data

Dec. 27, 1995 [JP] Japan ..................... 7-340909

[51] Int. Cl.$^6$ ................. A61K 31/67; A61K 31/675; C07F 9/6553; C07F 9/6539
[52] U.S. Cl. ................. 514/95; 514/80; 514/81; 514/85; 514/92; 544/337; 548/113; 548/119; 549/6
[58] Field of Search .................. 514/85, 92, 95; 544/337; 548/119; 549/6

[56] References Cited

U.S. PATENT DOCUMENTS 4,971,957 11/1990 Tsutsumi et al. .
5,480,874 1/1996 Shoji et al. ..................... 514/80

FOREIGN PATENT DOCUMENTS 604 657 7/1994 European Pat. Off. .
7-188269 7/1995 Japan .
2 220 206 1/1990 United Kingdom .

*Primary Examiner*—Michael G. Ambrose
*Attorney, Agent, or Firm*—Sughrue, Mion, Zinn, Macpeak & Seas, PLLC

[57] ABSTRACT

A phosphonic diester derivative represented by the following formula (1):

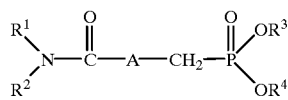

(1)

wherein $R^1$ represents a cycloalkyl group; a phenyl group which may have 1 to 3 substituents selected from the group consisting of a lower alkoxy group, a lower alkyl group, a halogen atom, a halogen-substituted lower alkyl group, a lower alkanoyl group, a nitro group, a benzoyl group, a cyano group, an N-lower alkylcarbamoyl group, an N-phenyl-lower alkylcarbamoyl group, an N-(halogen-substituted phenyl)carbamoyl group and an N,N-di-lower alkylcarbamoyl group; a 1,3,4-thiadiazol-2-yl group having a halogen-substituted lower alkyl group as a substituent; a thiazolyl group; a pyridyl group which may be substituted by a halogen atom; a benzothiazol-2-yl group having 1 to 2 lower alkoxy groups on the phenyl ring; or a 4,5-dihydrothieno[3,2-e]benzothiazol-2-yl group; $R^2$ represents a hydrogen atom or a phenyl lower alkyl group; $R^3$ and $R^4$ each represents a lower alkyl group; and A represents a heterocyclic ring selected from the group consisting of a pyrazine ring, a thiophene ring and a phenyl-substituted thiazole ring; the derivative being of value as an agent for treating and preventing hyperlipidemia, diabetes and cataract, or as an antitumor agent.

9 Claims, No Drawings

PHOSPHONIC DIESTER DERIVATIVES

TECHNICAL FIELD

The present invention relates to novel phosphonic diester derivatives.

BACKGROUND ART

The phosphonic diester derivatives of the invention are novel compounds not heretofore described in any literature.

The object of the invention is to provide compounds of value as medicines as will be described hereinafter.

DISCLOSURE OF THE INVENTION

The present invention provides a novel derivative represented by the following formula (1):

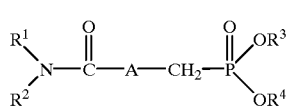

wherein $R^1$ represents a cycloalkyl group; a phenyl group which may have 1 to 3 substituents selected from the group consisting of a lower alkoxy group, a lower alkyl group, a halogen atom, a halogen-substituted lower alkyl group, a lower alkanoyl group, a nitro group, a benzoyl group, a cyano group, an N-lower alkylcarbamoyl group, an N-phenyl-lower alkylcarbamoyl group, an N-(halogen-substituted phenyl)carbamoyl group and an N,N-di-lower alkylcarbamoyl group; a 1,3,4-thiadiazol-2-yl group having a halogen-substituted lower alkyl group as a substituent; a thiazolyl group; a pyridyl group which may be substituted by a halogen atom; a benzothiazol-2-yl group having 1 to 2 lower alkoxy groups on the phenyl ring; or a 4,5-dihydrothieno[3,2-e]benzothiazol-2-yl group; $R^2$ represents a hydrogen atom or a phenyl lower alkyl group; $R^3$ and $R^4$ each represents a lower alkyl group; and A represents a heterocyclic ring selected from the group consisting of a pyrazine ring, a thiophene ring and a phenyl-substituted thiazole ring.

Each of the groups in the above formula (1) includes the following exemplary species.

The cycloalkyl group includes cyclopropyl, cyclobutyl, cyclopentyl, cyclohexyl, cycloheptyl, cyclooctyl and like $C_{3-8}$ cycloalkyl groups.

The lower alkyl group includes methyl, ethyl, propyl, isopropyl, butyl, isobutyl, tert-butyl, pentyl, hexyl and like $C_{1-6}$ straight- or branched-chain alkyl groups.

The lower alkoxy group includes methoxy, ethoxy, propoxy, butoxy, tert-butoxy, pentyloxy, hexyloxy and like $C_{1-6}$ straight- or branched-chain alkoxy groups.

The halogen atom includes fluorine, chlorine, bromine and iodine.

The halogen-substituted lower alkyl group includes the above lower alkyl groups having 1 or more halogen atoms as substituents, such as trifluoromethyl, pentafluoroethyl, heptafluoropropyl, nonafluorobutyl, undecafluoropentyl and tridecafluorohexyl.

The lower alkanoyl group includes acetyl, propionyl, butyryl, valeryl, pivaloyl, hexanoyl, heptanoyl and like $C_{2-7}$ alkanoyl groups.

The N-lower alkylcarbamoyl group includes N-methylcarbamoyl, N-ethylcarbamoyl, N-propylcarbamoyl, N-butylcarbamoyl, N-pentylcarbamoyl, N-hexylcarbamoyl and the like.

The N-phenyl-lower alkylcarbamoyl group includes N-benzylcarbamoyl, N-(2-phenylethyl)carbamoyl, N-(3-phenylpropyl)carbamoyl, N-(4-phenylbutyl)carbamoyl, N-(5-phenylpentyl)carbamoyl, N-(6-phenylhexyl) carbamoyl and the like.

The N-(halogen-substituted phenyl)carbamoyl group includes N-(4-chlorophenyl)carbamoyl, N-(3-chlorophenyl) carbamoyl, N-(2-chlorophenyl)carbamoyl, N-(4-fluorophenyl)carbamoyl, N-(4-bromophenyl)carbamoyl, N-(4-iodophenyl)carbamoyl and the like.

The N,N-di-lower alkylcarbamoyl group includes N,N-dimethylcarbamoyl, N,N-diethylcarbamoyl, N,N-dipropylcarbamoyl, N,N-dibutylcarbamoyl, N,N-dipentylcarbamoyl, N,N-dihexylcarbamoyl, N-methyl-N-ethylcarbamoyl and the like.

The phenyl lower alkyl group includes benzyl, 1-phenylethyl, 2-phenylethyl, 3-phenylpropyl, 4-phenylbutyl, 5-phenylpentyl, 6-phenylhexyl and the like.

The thiazolyl group includes 2-thiazolyl, 4-thiazolyl and 5-thiazolyl.

The 1,3,4-thiadiazol-2-yl group having a halogen-substituted lower alkyl group includes 5-trifluoromethyl-1,3,4-thiadiazol-2-yl, 5-pentafluoroethyl-1,3,4-thiadiazol-2-yl, 5-heptafluoropropyl-1,3,4-thiadiazol-2-yl, 5-nonafluorobutyl-1,3,4-thiadiazol-2-yl, 5-undecafluoropentyl-1,3,4-thiadiazol-2-yl, 5-tridecafluorohexyl-1,3,4-thiadiazol-2-yl and the like.

The pyridyl group which may be substituted by a halogen atom includes 2-pyridyl, 3-pyridyl, 4-pyridyl, 5-bromo-2-pyridyl, 5-chloro-2-pyridyl, 5-fluoro-2-pyridyl, 5-iodo-2-pyridyl, 5-bromo-3-pyridyl, 3-bromo-4-pyridyl and the like.

The benzothiazol-2-yl group having 1 to 2 lower alkoxy groups on the phenyl ring includes 4-methoxybenzothiazol-2-yl, 5-methoxybenzothiazol-2-yl, 6-methoxybenzothiazol-2-yl, 7-methoxybenzothiazol-2-yl, 4-ethoxybenzothiazol-2-yl, 4-propoxybenzothiazol-2-yl, 4-butoxybenzothiazol-2-yl, 4-pentyloxybenzothiazol-2-yl, 4-hexyloxybenzothiazol-2-yl, 4,6-dimethoxybenzothiazol-2-yl, 4,7-dimethoxybenzothiazol-2-yl, 5,7-dimethoxybenzothiazol-2-yl, 5,6-dimethoxybenzothiazol-2-yl, 4,6-diethoxybenzothiazol-2-yl, 4,6-dipropoxybenzothiazol-2-yl and the like.

The phenyl group which may have 1 to 3 substituents selected from the group consisting of a lower alkoxy group, a lower alkyl group, a halogen atom, a halogen-substituted lower alkyl group, a lower alkanoyl group, a nitro group, a benzoyl group, a cyano group, an N-lower alkylcarbamoyl group, an N-phenyl lower alkylcarbamoyl group, an N-(halogen-substituted phenyl)carbamoyl group and an N,N-di-lower alkylcarbamoyl group includes a phenyl group and the following substituted phenyl groups:

4-methoxyphenyl, 3-methoxyphenyl, 2-methoxyphenyl, 4-ethoxyphenyl, 4-propoxyphenyl, 4-butoxyphenyl, 4-pentyloxyphenyl, 4-hexyloxyphenyl, 4-fluorophenyl, 4-iodophenyl, 4-chlorophenyl, 4-bromophenyl, 2-chlorophenyl, 3-chlorophenyl, 4-methylphenyl, 3-methylphenyl, 2-methylphenyl, 4-ethylphenyl, 4-propylphenyl, 4-butylphenyl, 4-pentylphenyl, 4-hexylphenyl, 4-trifluoromethylphenyl, 3-trifluoromethylphenyl, 2-trifluoromethylphenyl, 4-pentafluoroethylphenyl, 4-heptafluoropropylphenyl, 4-nonafluorobutylphenyl, 4-undecafluoropentylphenyl, 4-tridecafluorohexylphenyl, 2-acetylphenyl, 3-acetylphenyl, 4-acetylphenyl, 2-propionylphenyl, 2-butyrylphenyl, 2-valerylphenyl, 2-pivaloylphenyl, 2-hexanoylphenyl, 2-heptanoylphenyl, 2-nitrophenyl, 3-nitrophenyl, 4-nitrophenyl, 2-benzoylphenyl, 3-benzoylphenyl, 4-benzoylphenyl, 4-cyanophenyl, 3-cyanophenyl, 2-cyanophenyl, 4-(N-methylcarbamoyl)phenyl, 3-(N-methylcarbamoyl)phenyl, 2-(N-methylcarbamoyl)phenyl, 2-(N-ethylcarbamoyl)phenyl, 2-(N-propylcarbamoyl) phenyl, 2-(N-butylcarbamoyl)phenyl, 2-(N-pentylcarbamoyl)phenyl, 2-(N-hexylcarbamoyl)phenyl, 2-(N-benzylcarbamoyl)phenyl, 3-(N-benzylcarbamoyl) phenyl, 4-(N-benzylcarbamoyl)phenyl, 2-[N-(2-phenylethyl)carbamoyl]phenyl, 2-[N-(4-chlorophenyl) carbamoyl]phenyl, 2-[N-(2-chlorophenyl)-carbamoyl] phenyl, 3-[N-(4-chlorophenyl)carbamoyl]phenyl, 4-[N-(4-chlorophenyl)carbamoyl]phenyl, 2-[N-(4-bromophenyl) carbamoyl]phenyl, 4-(N,N-dimethylcarbamoyl)-phenyl, 3-(N,N-dimethylcarbamoyl)phenyl, 2-(N,N-dimethylcarbamoyl)phenyl, 2-(N,N-diethylcarbamoyl) phenyl, 2-(N,N-dipropylcarbamoyl)phenyl, 2-(N,N-dibutylcarbamoyl)phenyl, 2-(N,N-dipentylcarbamoyl) phenyl, 2-(N,N-dihexylcarbamoyl)phenyl, 2-(N-methyl-N-ethylcarbamoyl)phenyl, 4-chloro-2-methylphenyl, 4-bromo-2-methylphenyl, 2-chloro-4-methylphenyl, 2-bromo-4-methylphenyl, 2-acetyl-4-chlorophenyl, 2-acetyl-4-bromophenyl, 4-acetyl-2-chlorophenyl, 4-acetyl-2-bromophenyl, 2-benzoyl-4-chlorophenyl, 2-benzoyl-4-bromophenyl, 4-benzoyl-2-chlorophenyl, 4-benzoyl-2-bromophenyl, 2-chloro-4-cyanophenyl, 4-chloro-2-cyanophenyl, 2-bromo-4-cyanophenyl, 4-bromo-2-cyanophenyl, 5-chloro-2-(N-methylcarbamoyl)phenyl, 5-bromo-2-(N-methylcarbamoyl)phenyl, 4-bromo-2-(N,N-dimethylcarbamoyl)phenyl, 4-chloro-2-(N,N-dimethylcarbamoyl)phenyl, 3,4-dimethoxyphenyl, 3,4,5-trimethoxyphenyl, 2,5-dichlorophenyl, 2-(N-methylcarbamoyl)-4-nitrophenyl, 2-(N-methylcarbamoyl)-5-nitrophenyl, 3-chloro-2-(N-methylcarbamoyl)phenyl, 3-bromo-2-(N-methylcarbamoyl)phenyl, 2-(N-benzylcarbamoyl)-3-chlorophenyl, 2-(N-benzylcarbamoyl)-3-bromophenyl, 2-(N-benzylcarbamoyl)-5-chlorophenyl, 2-(N-benzylcarbamoyl)-5-bromophenyl, 3,5-dichloro-2-(N-methylcarbamoyl)phenyl, 3,5-dibromo-2-(N-methylcarbamoyl)phenyl, 4,5-dichloro-2-(N-methylcarbamoyl)phenyl, 3-chloro-2-[N-(4-chlorophenyl) carbamoyl]phenyl, 5-chloro-2-[N-(4-chlorophenyl) carbamoyl]phenyl, 3-bromo-2-[N-(4-chlorophenyl) carbamoyl]phenyl,2-[N-( 4-bromophenyl)carbamoyl]-3-chlorophenyl, 2-methoxy-6-(N-methylcarbamoyl)phenyl, 2-ethoxy-6-(N-methylcarbamoyl)phenyl, 4-methoxy-2-(N-methylcarbamoyl)phenyl, 2-acetyl-3,5-dichlorophenyl, 2-acetyl-3,5-dibromophenyl, 2,4,6-trimethylphenyl, 3,5-di-t-butyl-4-methoxyphenyl, 2-cyano-3,5-dibromophenyl, 3,5-dibromo-2-(N,N-dimethylcarbamoyl)phenyl, 2-acetyl-3-bromo-5-chlorophenyl and the like.

The phosphonic diester derivatives of the formula (1) have hypolipidemic activity, hypoglycemic activity, cachexia ameliorating and treating activity, and cataract preventing and treating activity. The derivatives are useful as therapeutic and preventive agents for hyperlipidemia, diabetes and cataract, or as antitumor agents. In particular, the derivatives of the invention, which are highly soluble in water, can be readily formulated into solutions suitable for administration. Further, the derivatives have a feature of having less side effect.

Examples of the derivatives of the invention which are suitable for use as the above medicines are (a) compounds of the formula (1) wherein $R^2$ is a hydrogen atom, (b) the above compounds (a) wherein A is a thiophene ring, and (c) the above compounds (b) wherein $R^1$ is a 1,3,4-thiadiazol-2-yl group having a halogen-substituted lower alkyl group as a substituent, a thiazolyl group, a benzothiazol-2-yl group having one lower alkoxy group on the phenyl ring, a 4,5-dihydrothieno[3,2-e] benzothiazol-2-yl group or a phenyl group which has a halogen group as a substituent and which may further have a substituent selected from the group consisting of a lower alkanoyl group, a cyano group and an N,N-di-lower alkylcarbamoyl group.

Among the above compounds, diethyl 5-[(N-(2-acetyl-4-chlorophenyl)carbamoyl]-2-thienylmethyl-phosphonate is particularly preferred.

The process for preparing the phosphonic diester derivatives of the invention is described below in detail.

The derivatives of the invention can be prepared, for example, according to the process illustrated by the following reaction scheme.

Reaction scheme

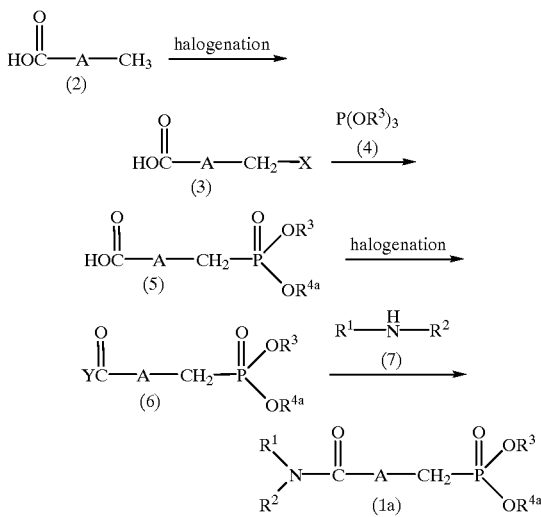

wherein $R^1$, $R^2$, $R^3$ and A are as defined above, $R^{4a}$ is the same as $R^3$, and X and Y each represents a halogen atom.

In the reaction scheme, the halogenation of the compound (2) can be carried out in an inert solvent such as benzene or carbon tetrachloride in the presence of a catalyst such as benzoyl peroxide, azobisisobutyronitrile (AIBN) or tert-butylhydroperoxide using a halogenating agent such as N-bromosuccinimide, N-chlorosuccinimide or bromine. The halogenating agent is usually used in a proportion of 1 to about 1.1 moles per mole of the compound (2). The reaction can be usually carried out at a temperature ranging from about 50° C. to the boiling point of the solvent and is completed in a period of about 5 to 20 hours.

The reaction between the resulting compound (3) and trialkyl phosphite (4) is carried out preferably without using any solvent, or may be carried out in a solvent which does not adversely affect the reaction, such as a lower alcohol, an aromatic or aliphatic hydrocarbon or dimethylformamide (DMF). The compound (4) is used in a proportion of 1 to about 5 moles per mole of the compound (3). The reaction temperature is preferably about 130 to 180° C. The reaction time is usually about 0.5 to 3 hours.

The subsequent halogenation of the resulting compound (5) can be carried out by a conventional process for preparing an acid halide. For this reaction, usable solvents are diethyl ether, tetrahydrofuran (THF), dichloromethane, chloroform, benzene and like inert solvents, and usable halogenating agents include phosphorus pentachloride, phosphorus oxychloride, sulfuryl chloride, oxalyl chloride and thionyl chloride. Preferably, the reaction is carried out at a temperature ranging from room temperature to the boiling point of the solvent and is completed in a period of about 1 to 5 hours.

The resulting compound (6) is reacted with an amine (7) to obtain the desired compound (1a) of the invention. The reaction is carried out using a deacidifying agent such as triethylamine, diethylaniline, N-methylmorpholine, pyridine, 4-dimethylaminopyridine or like tertiary amine in an inert solvent at a temperature ranging from room temperature to the boiling point of the solvent for about 0.5 to 10 hours. Examples of the inert solvent include benzene, toluene, diethyl ether, THF, 1,2-dimethoxyethane and dichloromethane. Each of the amine (7) and the deacidifying agent is used usually in an equimolar to excess proportion relative to the compound (6).

The desired compound obtained by the process of the above reaction scheme can be easily isolated and purified by a conventional isolation procedure. Examples of such procedure are adsorption chromatography, preparative thin-layer chromatography, recrystallization and solvent extraction.

The pharmaceutical composition containing the compound of the invention as an active ingredient is made into usual dosage forms of pharmaceutical compositions using pharmaceutically acceptable carriers, and used. Useful pharmaceutically acceptable carriers include various conventional diluents or excipients such as fillers, extenders, binders, humectants, disintegrators, surfactants and lubricants. These diluents or excipients are selected according to the unit dosage form of the pharmaceutical composition.

The pharmaceutical composition can be provided in a variety of unit dosage forms according to the intended medical treatment. Typical examples are tablets, pills, powders, solutions, suspensions, emulsions, granules, capsules, suppositories and injections (solutions, suspensions, etc.).

The tablets can be made using, as pharmaceutically acceptable carriers, excipients such as lactose, sucrose, sodium chloride, glucose, urea, starch, calcium carbonate, kaolin, crystalline cellulose, silicic acid and potassium phosphate, binders such as water, ethanol, propanol, simple syrup, glucose syrup, starch solutions, gelatin solutions, carboxymethyl cellulose, hydroxypropyl cellulose, methyl cellulose and polyvinylpyrrolidone, disintegrators such as carboxymethyl cellulose sodium, carboxymethyl cellulose calcium, low-substituted hydroxypropyl cellulose, dry starch, sodium alginate, agar powder, laminaran powder, sodium hydrogen carbonate and calcium carbonate, surfactants such as polyoxyethylene sorbitan fatty acid esters, sodium lauryl sulfate and stearyl monoglyceride, disintegration inhibitors such as sucrose, stearin, cacao butter and hydrogenated oil, absorption promoters such as quaternary ammonium bases and sodium lauryl sulfate, humectants such as glycerin and starch, adsorbents such as starch, lactose, kaolin, bentonite and colloidal silica, and lubricants such as purified talc, stearic acid salts, boric acid powder and polyethylene glycol. The tablets can be coated, if necessary, to provide sugar-coated tablets, gelatin-coated tablets, enteric tablets or film-coated tablets, or can be processed into double-layer or multi-layer tablets.

The pills can be prepared using, as pharmaceutically acceptable carriers, excipients such as glucose, lactose, starch, cacao butter, hydrogenated vegetable oil, kaolin and talc, binders such as gum arabic powder, tragacanth powder, gelatin and ethanol, disintegrators such as laminaran and agar, and the like.

The suppositories can be prepared using, as pharmaceutically acceptable carriers, polyethylene glycol, cacao butter, higher alcohols and their esters, gelatin, semisynthetic glyceride, and the like.

The capsules can be prepared in a conventional manner by blending the active ingredient compound of the invention with pharmaceutically acceptable carriers as mentioned above and filling the resulting mixture into hard gelatin capsule shells, soft capsule shells or the like.

When the compound of the invention is to be formulated into an injection such as a solution, emulsion or suspension, the injection is preferably sterilized and rendered isotonic with the blood. Useful diluents for preparing the injection include water, ethyl alcohol, macrogol, propylene glycol, ethoxylated isostearyl alcohol, polyoxylated isostearyl alcohol and polyoxyethylene sorbitan fatty acid esters. A sufficient amount of sodium chloride, glucose or glycerin may be added to the pharmaceutical composition to provide an isotonic solution. Conventional solubilizers, buffers, soothing agents, etc. can be also added.

Further, coloring agents, preservatives, fragrances, flavors, sweeteners or other pharmaceutically active substances can be optionally incorporated in the pharmaceutical compositions in various dosage forms.

The administration method for the above pharmaceutical composition is not limited. Thus, a proper method can be selected according to the particular dosage form, patient's age, sex and other conditions, severity of disease, and other factors. For example, the tablets, pills, solutions, suspensions, emulsions, granules and capsules are orally administered. The injection is intravenously administered singly or as a mixture with glucose, amino acid or like conventional infusions, or, if necessary, administered singly by the intramuscular, intradermal, subcutaneous or intraperitoneal route. The suppositories are administered rectally.

The proportion of the active ingredient compound of the formula (1) of the invention in the pharmaceutical composition is not critical but can be suitably selected from a broad range. However, it is generally preferable that the active ingredient compound accounts for about 1 to 70 wt. % of the pharmaceutical composition.

The dosage of the pharmaceutical composition can be selected according to the administration method, patient's age, sex and other conditions, severity of disease and other factors. Usually, however, it is preferable that the dosage of the compound of the invention as the active ingredient is about 0.5 to 20 mg per kg body weight a day, and this dosage can be administered in 1 to 4 divided doses.

BEST MODE FOR CARRYING OUT THE INVENTION

To illustrate the invention in further detail, preparation examples of the compounds of the invention are given below as Examples. Also given are Pharmacological Test Examples and Formulation Examples of the compounds of the invention.

Example 1

Preparation of diethyl 5-[N-4-methoxyphenyl)carbamoyl]-2-thienylmethylphosphonate In 840 ml of carbon tetrachloride were suspended 100 g of 5-methyl-2-thiophenecarboxylic acid, 125.2 g of N-bromosuccinimide and 7 g of benzoyl peroxide. The suspension was heated to 90° C. with vigorous agitation. After the reaction started, the reaction temperature was raised to 100° C. and agitation was continued for 2 hours at the same temperature. The reaction mixture was cooled to 0°

C., and 500 ml of n-hexane was added thereto. Precipitated crystals were collected by filtration and washed with 100 ml of n-hexane. The obtained crude crystals were suspended in 2 of water and the suspension was stirred at room temperature for 10 minutes. The suspended crystals were collected again by filtration and washed with 200 ml of water. The obtained crystals were recrystallized from ethanol-water to give 84 g of the desired 5-bromomethyl-2-thiophenecarboxylic acid as colorless crystals.

189 g of triethyl phosphite was added to 84 g of 5-bromomethyl-2-thiophenecarboxylic acid obtained above, and the mixture was stirred with heating at 160° C. for 1 hour. The reaction mixture was dissolved in 200 ml of ethanol, and 190 ml of a 4N aqueous solution of sodium hydroxide was slowly added dropwise with ice-cooling and stirring. After stirring the resulting mixture at room temperature for 12 hours, 200 ml of dichloromethane was added for separating the reaction mixture. The obtained aqueous layer was mixed with 300 ml of a 30% aqueous solution of hydrochloric acid and subjected to extraction with chloroform. The chloroform layer was dried over anhydrous magnesium sulfate. Then, the solvent was distilled off under reduced pressure, giving 95 g of 5-[(diethoxyphosphoryl)methyl]-2-thiophenecarboxylic acid as colorless crystals having a melting point of 77-78° C.

12 g of thionyl chloride was added to 5.6 g of the above obtained 5-[(diethoxyphosphoryl)methyl]-2-thiophenecarboxylic acid, and the mixture was stirred at room temperature for 4 hours. Excess thionyl chloride was distilled off from the reaction mixture under reduced pressure, giving 5.8 g of 5-[(diethoxyphosphoryl)methyl]-2-thiophenecarbonyl chloride as an oil.

2.46 g of 4-methoxyaniline and 20 ml of pyridine were dissolved in 20 ml of dry dichloromethane. A solution of 5.80 g of 5-[(diethoxyphosphoryl)methyl]-2-thiophenecarbonyl chloride in 20 ml of dry dichloromethane was added dropwise to the above solution with ice-cooling and stirring. The resulting mixture was stirred at room temperature for 12 hours, mixed with 50 ml of a 10% aqueous solution of hydrochloric acid, and subjected to extraction with chloroform. The chloroform layer was washed with 50 ml of water and dried over anhydrous magnesium sulfate. The solvent was distilled off under reduced pressure. The residue was subjected to silica gel column chromatography (eluent: chloroform-ethyl acetate= 1:1). The obtained crude crystals were recrystallized from dichloromethane-n-hexane, giving 3.0 g of the desired compound as colorless crystals.

The obtained compound will be referred to as Compound 1, and the structure and melting point of Compound 1 are shown in Table 1. Examples 2 to 28

The desired compounds were prepared by following the procedure of Example 1. The obtained compounds will be referred to as Compounds 2 to 28, and the structures and melting points (or NMR data when the obtained compound was an oil) of the obtained compounds are shown in Table 1.

TABLE 1

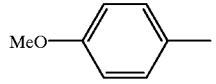

Me = methyl group, Et = ethyl group, Ph = phenyl group,
Bn = benzyl group, Ac = acetyl group, Bz = benzoyl group

| No. | $R^1$ | $R^2$ | $R^3 = R^4$ | A | Mp (° C.) |
|---|---|---|---|---|---|
| 1 | 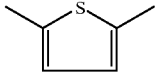 | H | Et | 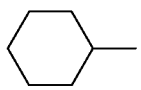 | 146~147 |
| 2 | 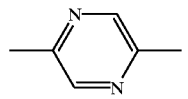 | H | Et | 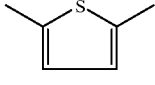 | 114~115 |
| 3 | Ph | H | Et | 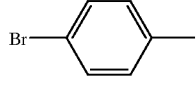 | 151~152 |
| 4 | 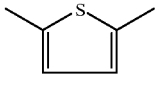 | H | Et | | 168~171 |

TABLE 1-continued

| | | | | | |
|---|---|---|---|---|---|
| 5 | 4-Cl-C6H4-CH2- | Bn | Et | 2,5-dimethylthiophene | Oil |
| 6 | 4-F3C-C6H4-CH2- | H | Et | 2,5-dimethyl-4-phenylthiazole | 178~179 |
| 7 | 5-Cl-2-Me-C6H3(Me)-CH2- | H | Et | 2,5-dimethylpyrazine | 142.5~143.5 |
| 8 | 5-Cl-2-Me-C6H3(Ac)-CH2- | H | Et | 2,5-dimethylthiophene | 115~116 |
| 9 | 5-Cl-2-Me-C6H3(Bz)-CH2- | H | Et | 2,5-dimethylthiophene | Oil |
| 10 | 5-Br-2-Me-C6H3(CN)-CH2- | H | Et | 2,5-dimethylthiophene | 155~156 |
| 11 | 3-Br-4-Me-C6H3(CN)- | H | Et | 2,5-dimethylthiophene | 110~111 |
| 12 | 4-Cl-2-Me-C6H3(CONHMe)-CH2- | H | Et | 2,5-dimethylthiophene | 177~178.5 |
| 13 | 4-Cl-2-Me-C6H3(CONHMe)-CH2- | H | Et | 2,5-dimethylpyrazine | 171~172 |

TABLE 1-continued
| | | | | | |
|---|---|---|---|---|---|
| 14 | 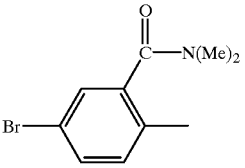 | H | Et | 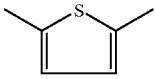 | 135~137 |
| 15 | 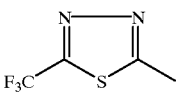 | H | Et | 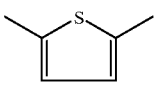 | 169~172 |
| 16 | 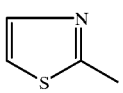 | H | Et | 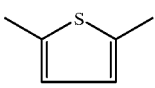 | 128~130 |
| 17 | 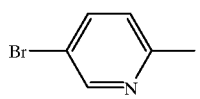 | H | Et | 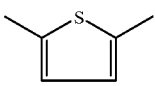 | 156~158 |
| 18 | 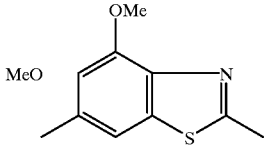 | H | Et | 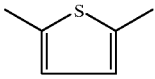 | 221.5~223.5 |
| 19 | 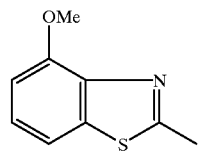 | H | Et | 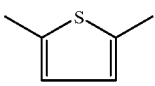 | 231~233 |
| 20 | 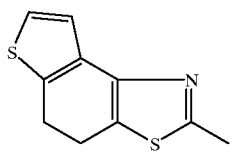 | H | Et | 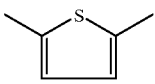 | 180~182 |
| 21 | 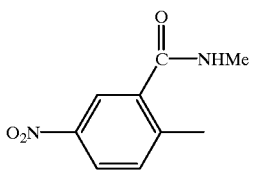 | H | Et | 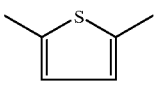 | 207~210 |
| 22 | 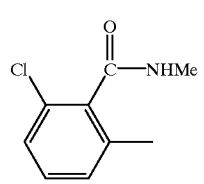 | H | Et | 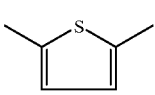 | 144~145 |
| 23 | 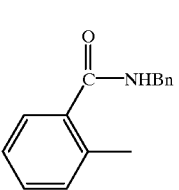 | H | Et | 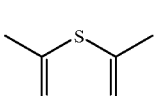 | 146~148 |

TABLE 1-continued

| No. | Structure | | | Ring | mp (°C) |
|---|---|---|---|---|---|
| 24 | 2,4-dichloro-6-methylbenzoyl-NHMe | H | Et | 2,5-dimethylthiophene | 152~154 |
| 25 | 2-chloro-6-methyl-N-(4-chlorophenyl)benzamide | H | Et | 2,5-dimethylthiophene | 153~154 |
| 26 | 2-methyl-3-methoxy-N-methylbenzamide | H | Et | 2,5-dimethylthiophene | 155~158 |
| 27 | 2-methyl-4-nitro-N-methylbenzamide | H | Et | 2,5-dimethylthiophene | 183~185 |
| 28 | 2-methylpyridine | H | Et | 2,5-dimethylpyrazine | 104.5~105.5 |

$^{1}$H-NMR (CDCl$_{3}$; Internal standard = TMS)
No.   Result of analysis (δ value; ppm)

5    1.25(6H, t, J=7.1Hz), 3.22(2H, d, J=21.3Hz), 4.0–4.1(4H, m),
     5.00(2H, s), 6.7–6.8(2H, m), 6.98(2H, dd, J=2.2, 6.7Hz), 7.2–7.3(7H, m)
9    1.31(6H, t, J=7.0Hz), 3.39(2H, d, J=21.3Hz), 4.1–4.2(4H, m),
     7.0–7.2(1H, m), 7.5–7.7(8H, m), 8.77(1H, dd, J=1.9, 7.6Hz), 11.78(1H, s)

In addition to the compounds illustrated in the Examples, the following are typical species of the compound of the invention.

Dimethyl 5-[N-(2-acetyl-4-chlorophenyl)carbamoyl]-2-thienylmethylphosphonate

Diisopropyl 5-[N-(2-acetyl-4-chlorophenyl)carbamoyl]-2-thienylmethylphosphonate

Ethyl, methyl 5-[N-(2-acetyl-4-chlorophenyl)carbamoyl]-2-thienylmethylphosphonate Diethyl 5-[N-(2-acetyl-4-bromophenyl)carbamoyl]-2-thienylmethylphosphonate Diethyl 5-[N-(2-acetyl-4-chlorophenyl)carbamoyl]-4-phenyl-2-thiazolylmethylphosphonate Diethyl 5-[N-(2-acetyl-4-chlorophenyl)carbamoyl]-2-pyradinylmethylphosphonate Diethyl 5-(N-cyclohexylcarbamoy)-2-thienylmethylphosphonate Diethyl 5-[N-(4-trifluoromethylphenyl)carbamoyl]-2-thienylmethylphoate Diethyl 5-[N-(4-chloro-2-methylphenyl)carbamoyl]-2-thienylmethylphosphonate Diethyl 5-[N-(4-bromo-2-cyanophenyl)carbamoyl]-2-pyradinylmethylphosphonate Diethyl 5-[N-(4-bromo-2-cyanophenyl)carbamoyl]-4-phenyl-2-thiazolylmethylphosphonate Diethyl 5-[N-[4-bromo-2-(N,N-dimethylcarbamoyl)phenyl]-carbamoyl]-2-pyradinylmethylphosphonate Diethyl 5-[N-[4-bromo-2-(N,N-dimethylcarbamoyl)phenyl]carbamoyl]-4-phenyl-2-thiazolylmethylphosphonate Diethyl 5-[N-(4,5-dihydrothieno[3,2-e]benzothiazol-2-yl)carbamoyl]-2-pyradinylmethylphosphonate Diethyl 5-[N-4,5-dihydrothieno[3,2-e]benzothiazol-2-yl)-carbamoyl]-4-phenyl-2-thiazolylmethylphosphonate Diethyl 4-[N-2-acetyl-4-chlorophenyl)carbamoyl]-2-thienylmethylphosphonate Diethyl 5-[N-(2-acetyl-4-chlorophenyl)carbamoyl]-3-thienylmethylphosphonate Diethyl 4-[N-(2-acetyl-4-chlorophenyl)carbamoyl]-3-thienylmethylphosphonate Diethyl 4-(N-(2-acetyl-4-chlorophenyl)carbamoyl]-5-phenyl-2-thiazolylmethylphosphonate Diethyl 6-(N-(2-acetyl-4-chlorophenyl)carbamoyl]-2-pyradinylmethylphosphonate Diethyl 5-[N-(4-methoxybenzothiazol-2-yl)carbamoyl]-2-pyradinylmethylphosphonate Diethyl 5-[N-(4-methoxybenzothiazol-2-yl)carbamoyl]-4-phenyl-2-thiazolylmethylphosphonate Diethyl 5-[N-(4-acetyl-2-chlorophenyl)carbamoyl]-2-thienylmethylphosphonate Diethyl 5-[N-(2-acetyl-4-fluorophenyl)carbamoyl]-2-thienylmethylphosphonate Diethyl 5-[N-(2-acetyl-4-iodophenyl)carbamoyl]-2-thienylmethylphosphonate Diethyl 5-[N-benzyl-N-(4-chlorophenyl)carbamoyl]-2-pyradinylmethylphosphonate Diethyl 5-[N-benzyl-N-(4-chlorophenyl)carbamoyl]-4-phenyl-2-thiazolylmethylphosphonate Diethyl 5-[N-(2-acetyl-4-chlorophenyl)-N-benzylcarbamoyl]-2-thienylmethylphosphonate Diethyl 5-[N-benzyl-N-(4-bromo-2-cyanophenyl)carbamoyl]-2-thienylmethylphosphonate Pharmacological Test Example 1

Using rats with Triton-induced hyperlipidemia, the therapeutic and preventive effect of the compound of the invention on hyperlipidemia was determined according to the method of Kuroda et al. [Biochem. Biophys. Acta., 489, 119 (1977)] as follows.

A solution of 300 mg/kg Triton (Triton WR 1339) in physiological saline was administered to 6 to 7-week-old male Wistar rats in groups of 5 (test groups) through the tail vain, and, at the same time, 100 mg/kg of the test compound suspended in a 0.5% carboxymethyl cellulose sodium (CMC-Na) solution was orally administered.

As a control group, a group of 5 rats given the above Triton solution were orally dosed with a 0.5% aqueous CMC-Na solution alone.

Twenty four hours after administration of Triton, blood was taken from the rats of the test groups and control group, and the plasma triglyceride (TG) level was determined using Triglyceride G-Test Wako (product of Wako Pure Chemical Industries, Ltd.).

The rate of reduction (%) in plasma TG level of the test groups was calculated according to the following equation. The test rats were fasted before Triton administration through completion of blood sampling but allowed free access to drinking water.

$$\text{Rate of reduction (\%) in plasma } TG \text{ level} = \left[1 - \frac{\text{(Test group value)}}{\text{(Control group value)}}\right] \times 100$$

Table 2 shows the results.

TABLE 2

| Test compound (Example No.) | Rate of reduction (%) in plasma TG level |
| --- | --- |
| 8 | 71 |
| 19 | 14 |
| 20 | 31 |

As apparent from Table 2, the test compounds according to the invention have TG reducing activity and are effective for preventing and treating hyperlipidemia.

Pharmacological Test Example 2

Using normal rats, the therapeutic and preventive effect of the compound of the invention on hyperlipidemia was determined by the following method.

A suspension of 100 mg/kg of the test compound in a 5% gum arabic solution was orally administered to 6 to 7-week-old male Wistar rats in groups of 5 (test groups) at 9 o'clock in the morning of the first day of the test and at 9 o'clock in the morning of the following day.

As a control group, a group of 5 rats were orally dosed with a 5% gum arabic solution.

Four hours after the final administration, blood was taken from the rats of the test groups and control group, and the plasma triglyceride (TG) level was determined using Triglyceride G-Test Wako (product of Wako Pure Chemical Industries, Ltd.).

The rate of reduction (%) in plasma TG level of the test groups was calculated according to the following equation. The test rats were fasted before the administration of the test compound through completion of blood sampling but allowed free access to drinking water.

$$\text{Rate of reduction (\%) in plasma } TG \text{ level} = \left[1 - \frac{\text{(Test group value)}}{\text{(Control group value)}}\right] \times 100$$

Table 3 shows the results.

TABLE 3

| Test compound (Example No.) | Rate of reduction (%) in plasma TG level |
| --- | --- |
| 4 | 10 |
| 10 | 28 |
| 14 | 14 |
| 15 | 37 |
| 16 | 17 |

As apparent from Table 3, the test compounds according to the invention have TG decreasing activity and are effective for preventing and treating hyperlipidemia.

Formulation Example 1 Preparation of Tablets

Using the compound obtained in Example 8 as an active ingredient, 2000 tablets each containing 250 mg of the active ingredient were prepared according to the following formula.

| | |
|---|---|
| Compound of Example 8 | 500 g |
| Lactose (according to Japanese pharmacopeia: JP) | 67 g |
| Corn starch (JP) | 33 g |
| Carboxymethyl cellulose calcium (JP) | 25 4 |
| Methyl cellulose (JP) | 12 g |
| Magnesium stearate (JP) | 3 g |
| Total | 640 g |

The compound of Example 8, lactose, corn starch and carboxymethyl cellulose calcium were well blended and granulated using an aqueous solution of methyl cellulose. The granulated mixture was passed through a 24-mesh sieve and the granules under the sieve were mixed with magnesium stearate and compression-molded into the desired tablets.

Formulation Example 2 Preparation of Capsules

Using the compound obtained in Example 8 as an active ingredient, 2000 hard gelatin capsules each containing 250 mg of the active ingredient were prepared according to the following formula.

| | |
|---|---|
| Compound of Example 8 | 500 g |
| Crystalline cellulose (JP) | 60 g |
| Corn starch (JP) | 34 g |
| Talc (JP) | 4 g |
| Magnesium stearate (JP) | 2 g |
| Total | 600 g |

Thus, the ingredients were finely pulverized and the powders obtained were blended to give a homogeneous mixture. The mixture was filled into proper-sized gelatin capsule shells for oral administration to provide the desired capsules.

We claim:

1. A phosphonic diester derivative represented by the following formula (1):

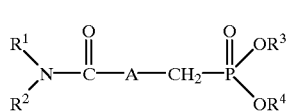

(1)

wherein $R^1$ represents a cycloalkyl group; a phenyl group which may have 1 to 3 substituents selected from the group consisting of a lower alkoxy group, a lower alkyl group, a halogen atom, a halogen-substituted lower alkyl group, a lower alkanoyl group, a nitro group, a benzoyl group, a cyano group, an N-lower alkylcarbamoyl group, an N-phenyl-lower alkylcarbamoyl group, an N-(halogen-substituted phenyl)carbamoyl group and an N,N-di-lower alkylcarbamoyl group; a 1,3,4-thiadiazol-2-yl group having a halogen-substituted lower alkyl group as a substituent; a thiazolyl group; a pyridyl group which may be substituted by a halogen atom; a benzothiazol-2-yl group having 1 to 2 lower alkoxy groups on the phenyl ring; or a 4,5-dihydrothieno[3,2-e]benzothiazol-2-yl group; $R^2$ represents a hydrogen atom or a phenyl lower alkyl group; $R^3$ and $R^4$ each represents a lower alkyl group; and A represents a heterocyclic ring selected from the group consisting of a pyrazine ring, a thiophene ring and a phenyl-substituted thiazole ring.

2. The phosphonic diester derivative according to claim 1 wherein $R^2$ is a hydrogen atom.

3. The phosphonic diester derivative according to claim 2 wherein A is a thiophene ring.

4. The phosphonic diester derivative according to claim 3 wherein $R^1$ is a 1,3,4-thiadiazol-2-yl group having a halogen-substituted lower alkyl group as a substituent, a thiazolyl group, a benzothiazol-2-yl group having one lower alkoxy group on the phenyl ring, a 4,5-dihydrothieno[3,2-e]benzothiazol-2-yl group or a phenyl group which has a halogen atom as a substituent and which may further have a substituent selected from the group consisting of a lower alkanoyl group, a cyano group and an N,N-di-lower alkylcarbamoyl group.

5. The phosphonic diester derivative according to claim 4 which is diethyl 5-[N-(2-acetyl-4-chlorophenyl)carbamoyl]-2-thienylmethylphosphonate.

6. A pharmaceutical composition for treating and preventing hyperlipidemia comprising an effective amount of the phosphonic diester derivative according to claim 1 and a pharmaceutically acceptable carrier.

7. A pharmactical composition for treating and preventing hyperlipidemia comprising an effective amount of the phosphonic diester derivative according to claim 4 and a pharmaceutically acceptable carrier.

8. A pharmaceutical composition for treating and preventing hyperlipidemia comprising an effective amount of the phosphonic diester derivative according to claim 5 and a pharmaceutically acceptable carrier.

9. A method of treatment or prevention of hyperlipidemia, comprising administering a therapeutically effective amount of the phosphonic diester derivative according to claim 1 to a subject in need thereof.

* * * * *